United States Patent [19]
Broude et al.

[11] Patent Number: 5,814,829
[45] Date of Patent: Sep. 29, 1998

[54] MULTISTATION SURFACE INSPECTION SYSTEM

[75] Inventors: Sergey V. Broude, Newton Centre; Nicholas Allen, Bedford; Abdu Boudour, West Newton; Eric Chase, Carlisle; Carl Johnson, Tewksbury; Pascal Miller, North Chelmsford; Jay Ormsby, Salem, all of Mass.

[73] Assignee: QC Optics, Inc., Wilmington, Mass.

[21] Appl. No.: 500,768

[22] Filed: Jul. 11, 1995

[51] Int. Cl.⁶ .................................................. G01N 21/88
[52] U.S. Cl. ........................... 250/559.46; 250/223 B; 250/559.41; 209/555
[58] Field of Search .......................... 250/559.4, 559.41, 250/559.42, 559.43, 559.44, 559.45, 559.46, 559.47, 223 B; 356/430, 431; 209/555, 556, 578, 579

[56] References Cited

U.S. PATENT DOCUMENTS

| | | | |
|---|---|---|---|
| 3,539,006 | 11/1970 | Hanna et al. | 209/555 |
| 3,684,385 | 8/1972 | Einfalt et al. | 250/223 B |
| 4,943,734 | 7/1990 | Johnson et al. | 250/559.41 |
| 5,127,726 | 7/1992 | Moran | 250/559.46 |

*Primary Examiner*—Edward P. Westin
*Assistant Examiner*—Kevin Pyo
*Attorney, Agent, or Firm*—Iandiorio & Teska

[57] ABSTRACT

An inspection system and an inspection method, the method including detecting flaws on a surface, determining the size, count, and position of flaws on the surface, providing a representation of the detected flaws by size, count, and position on a display, setting a display threshold value which is a function of a number of particles of a particular size to be displayed on the display, determining when the display threshold is breached and in response adjusting the display to cease displaying those flaws, storing at least one inspection threshold value, and determining when the inspection threshold value is breached and in response outputting an inspection interrupt signal to stop the inspection after the inspection threshold value is breached.

18 Claims, 10 Drawing Sheets

MULTISTATION SURFACE INSPECTION SYSTEM

FIELD OF INVENTION

A surface inspection system for detecting flaws and particles on a surface such as a photolithographic mask.

BACKGROUND OF INVENTION

Glass photolithographic masks or plates comprising a chrome surface pattern on a glass or quartz substrate are used in the manufacture of thousands of semi-conductor wafers during a production run using a "stepper" printing machine. Therefore, it is critical that the surface of the mask and the pellicle on the mask be free of contaminating particles lest the image of the particles be reproduced on each wafer during a production run. Accordingly, the masks are typically inspected for flaws before a production run using very precise equipment shown, for example, in U.S. Pat. Nos. 4,943,734; 4,794,264; 4,794,265; and 5,389,794 incorporated herein by reference.

As a mechanical mask holder/spindle assembly transports the mask, the surface of the mask is scanned by a laser beam directed to the surface and the scattering of the laser beam off the surface is analyzed: the scattering off the surface will be different if a flaw or particle is present than if no flaw or particle is present. The scattering can be analyzed to the point where particles or flaws are classified by size.

The applicant's prior surface inspection apparatus utilize various signal processing routines and computer programs to process and analyze the particle data (e.g., size and position) thereby providing the user with a computer generated map which shows the relative size and position of all particles on the mask. The user then uses a microscope to visually inspect any particles of interest. These prior systems, however, are not precise enough to detect very small particles (e.g. 0.3 microns in diameter). Applicants have invented a more precise inspection station but, being more precise, it is slower than the inspection station shown in U.S. Pat. No. 4,943,734, commercially available as the API-3000 sold by the assignee of the instant application, Q.C. Optics, Burlington, Mass. As the inspection time increases so does inspection cost. Therefore, it is important that inspection time is not wasted. Also, as the inspection precision increases, it becomes increasingly difficult to differentiate between small particles and noise and/or scattering indicative of the chrome surface pattern.

SUMMARY OF INVENTION

It is therefore an object of this invention to provide an efficient surface inspection system.

It is a further object of this invention to provide such a surface inspection system which utilizes a faster but less precise inspection station to initially inspect a photolithographic mask before subjecting the mask to a more precise but slower inspection station.

It is a further object of this invention to provide a surface inspection system which automatically monitors the inspection data, determines when a quality threshold is reached, and then automatically stops further inspection of the mask.

It is a further object of this invention to discriminate between diffraction of the inspection laser beam by the mask pattern and scattering of the inspection laser beam by actual flaws and particles on the mask.

It is a further object of this invention to provide an inspection system which discriminates between flaws of different sizes and automatically excludes flaws of certain sizes to prevent the display of noise.

It is a further object of this invention to provide such an inspection system which prevents the display of flaws of a particular size in particular positions.

This invention results from the realization that if the inspection of a photolithographic mask at any time and at any inspection station reveals that the quality of the mask is below a preset minimum, there is no need to continue the inspection of that mask and also that the system can be programmed to monitor the complete inspection process for a breach of the preset quality threshold and in response halt the inspection—automatically ceasing any further inspection at one station and/or interrupting a transfer from one station to another.

The invention results from the further realization that while the diffraction of an inspection laser beam by the mask pattern is a major source of noise in a photolithographic mask inspection system, this noise can be prevented from being recorded by presetting a maximum number of detectable flaws in each of several size categories. Once the maximum for a given size category is reached during an inspection procedure, a conclusion can be drawn that this size category corresponds not to flaws but to surface pattern scattering, and all flaws of this and lower size categories can be excluded from a displayed map of detected flaws. This exclusion is based on the assumption that the detection of a large number of defects of the same size is most likely actually surface pattern scattering.

This invention results from the further realization that if all of the flaws are plotted on the display of and presented for the operator's review, the operator can disable the display of certain particles of a particular size in order to manually discriminate between real defects and surface pattern noise based on the overall display appearance.

This invention features and depending on a specific application, may comprise, include, consist essentially of, or consist of a surface inspection system. There are means for detecting flaws on the surface, means for determining the size of any detected flaws, and means for counting the number of flaws of each size. Further included are means for determining the position of the flaws on the surface. An inspection and/or display threshold is stored and there are means for determining if the stored threshold value or values have been exceeded. In response, a signal is outputted either to a display controller or to the data collection routines and/or to the robot controller which maneuvers a surface under inspection between inspection stations.

The threshold value may be an inspection threshold value and then the outputted signal is an interrupt signal which stops surface inspection. If the threshold value is a display threshold value, the outputted signal adjust the display controller to limit display of a particular size of detected flaws.

In this way, the inspection at one station or further inspection in the system itself may be halted when an inspection threshold value is exceeded (e.g. too many flaws of a particular size) to save inspection time and to provide a very efficient surface inspection system. Also, the system automatically monitors the detection of flaws which may be indicative of noise and/or the surface pattern on the surface under inspection and in response adjust the display so that these non-flaws are not displayed. In general sense, when even a few large flaws are detected, the system automatically interrupts the inspection process to save inspection time since the mask under inspection is already determined to be below a quality threshold. On the other hand, a large number of detected flaws of a very small size is often most likely not surface flaws or particles at all, but instead noise and/or detection of the chrome pattern on the glass substrate. Accordingly, the system of this invention stops displaying those particles so that quality control personnel have a clear picture of the real flaws on the surface.

The surface inspection system of this invention has a plurality of inspection stations and there are means for translating a surface to be inspected to each station. There are means for storing at least one inspection threshold value, and means for determining if the inspection threshold value has been exceeded and in response for outputting an inspection interrupt signal. The inspection threshold value may be a function of at least one of the size, location, and the number of particles detected at one inspection station. The threshold value may be a function of at least one of the size, location, and number of particles detected at each inspection station. The inspection threshold value may also be a function of the number of particles of a particular size or of the particles' surface distribution density. There may be one or many preset inspection threshold values stored in computer memory. Typically the means for translating the surface between stations is programmable to translate the surface between the inspection stations in a predetermined order. The means for determining if the inspection threshold value has been exceeded may interrupt that predetermined order when the inspection threshold value is exceeded to prevent further inspection of a surface and to save time and therefore money since there is no need to engage in further inspection of a surface which is already has been determined to be below a quality threshold.

In the preferred embodiment, the inspection system of this invention has one station of a first sensitivity and a first inspection time and a second, higher resolution station of a higher sensitivity but a longer inspection time. The means for determining of this invention outputs an interrupt signal which prevents translation of a surface under inspection to the second station if the inspection threshold is breached during inspection at the first station and/or prevents further inspection at the second station if the inspection threshold is breached at any time during inspection at the second station.

This invention also features a surface inspection method comprising translating a surface to be inspected to a plurality of inspection stations, storing at least one inspection threshold value, and determining if the inspection threshold value has been exceeded and in response outputting an inspection interrupt signal.

As delineated above, another feature of this invention is the ability to adjust the display to cease display of flaws which meet a preset display threshold. There are means for detecting flaws on the surface; means for determining the size of detected flaws; means for counting the number of flaws of each size; means for determining the position of the flaws detected on the surface; a display and display control means for providing a representation of said detected flaws by size, count, and position on the display. There are means for setting the maximum number of detected flaws of a predetermined size to be displayed and means for determining if the maximum number is exceeded and in response adjusting the display control means to cease display of flaws of that predetermined size.

In a broader sense, this invention features an inspection system comprising means for detecting flaws on a surface, means for counting the number of flaws, and for determining the size of the flaws, and for determining and the position of the flaws and a display and display controls means for providing a representation of the detected flaws by size, count, and position on the display. There are means for setting the display threshold which is a function of at least one of the count of the flaws, the size of the flaws, and/or the position of the flaws and means for determining if the display threshold is exceeded. In response, the display control means is adjusted so that those flaws which exceed the display threshold are not displayed. The display threshold can be set before the inspection begins, during inspection, or after the inspection and even after all the flaws detected are displayed. The display threshold may be a preset count of flaws for a particular size and if so the means for determining ceases display of flaws of that predetermined size after the preset count is reached.

It is often desirable to closely monitor the number and size of flaws detected in a particular location. Accordingly, this invention features means for setting a limit on the number of particles of a particular size to be displayed in a particular location or locations and means for determining when the limit is reached and in response adjusting the display control means to cease displaying flaws in that particular location or locations.

This invention also features an inspection method comprising detecting flaws on a surface, determining the size of a detected flaws, counting the number of flaws of each size, determining the position of flaws detected on the surface, providing a representation of detected flaws by size, count, and position on a display, setting a maximum number of detected flaws for a predetermined size to be displayed, and determining if the maximum number is exceeded and in response ceasing display of flaws of a predetermined size. The display threshold may be a function of at least one of the count of the flaws, the size of the flaws, and the position of the flaws detected. The method then involves determining if the display threshold is exceeded and in response adjusting the display.

Finally, this invention features an inspection system comprising means for detecting flaws on a surface, means for determining the size, count, and position of flaws on the surface, a display and display control means for providing a representation of the detected flaws by size, count, and position on the display, means for setting a display threshold which is a function of the number of particles of a particular size to be displayed on the display; means for determining when the display threshold is breached; and in response for adjusting the display control means to cease displaying those flaws. Further included are means for storing at least one inspection threshold value and means for determining when the inspection threshold value is breached and in response outputting an inspection interrupt signal.

DISCLOSURE OF PREFERRED EMBODIMENT

Other objects, features and advantages will occur to those skilled in the art from the following description of a preferred embodiment and the accompanying drawings, in which.

As discussed in the background of invention above, photolithographic mask 10 includes a patterned area 12 protected by pellicle 14. Photolithographic mask 10 is formed of a glass or quartz substrate and has on one of its surfaces a plurality of chrome patterns 12. On its other surface, no patterns are generally formed. Most of these masks are between 4 to 8 inches in width and 4 to 8 inches in length with a thickness of approximately 0.09" to 0.25". There may be another protective pellicle (not shown) on the other side of photolithographic mask 10 as well.

Figure 1:
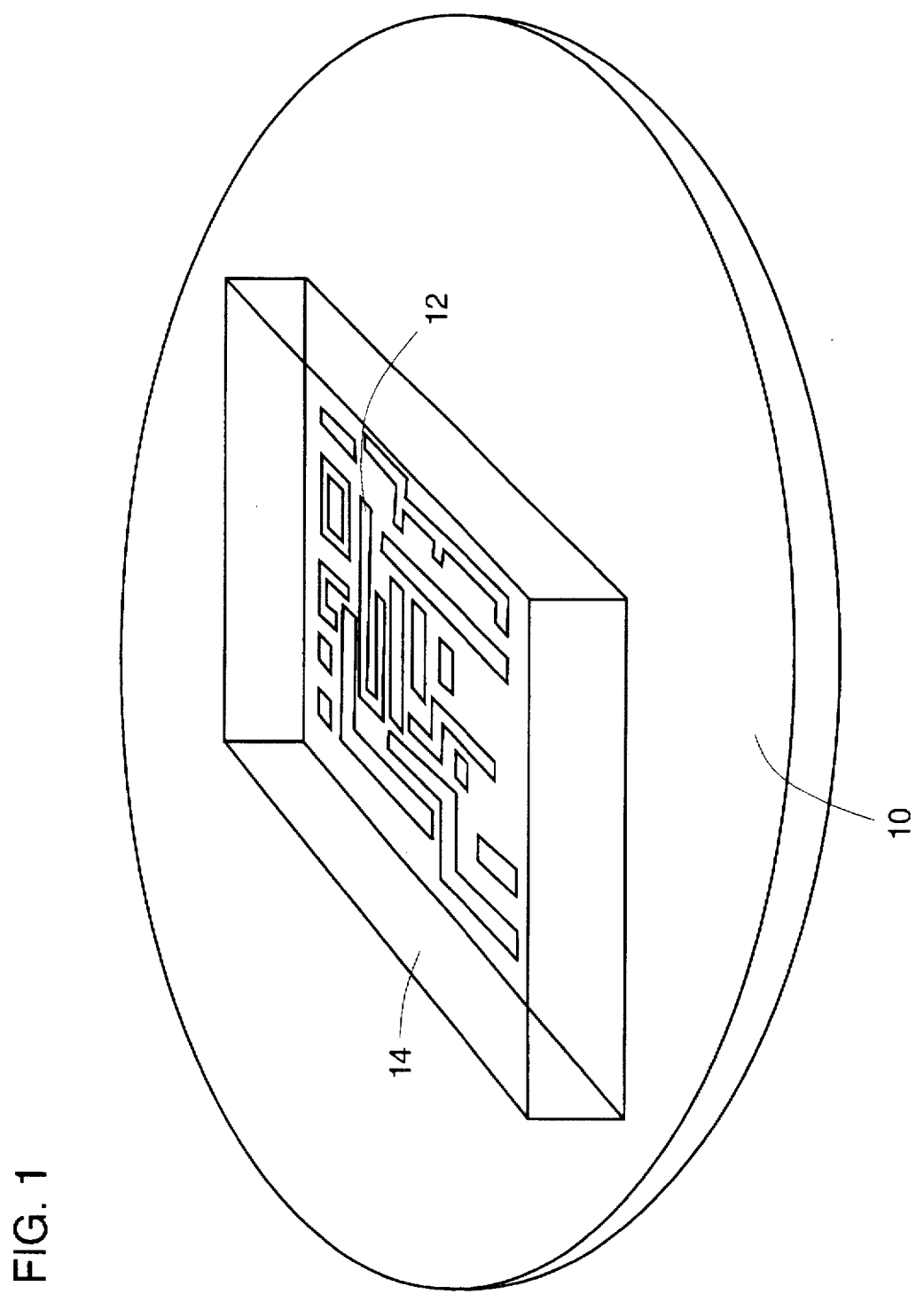
FIG. 1 is a three dimensional schematic view of a typical photolithographic mask representing a type of surface to be inspected in the surface inspection system of this invention.
Figure 2:
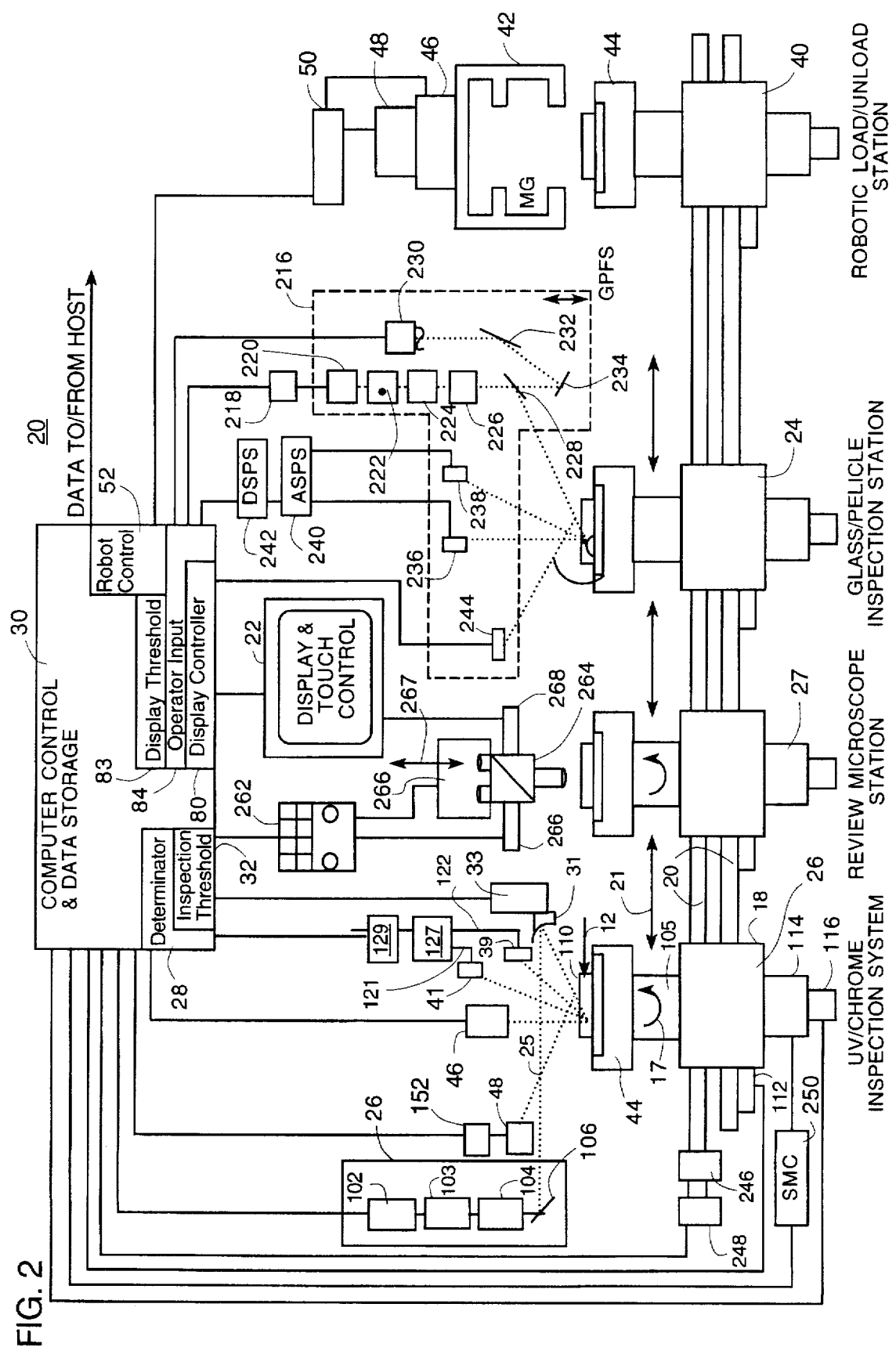
FIG. 2 is a schematic block diagram of the surface inspection system of this invention.
Figure 5:
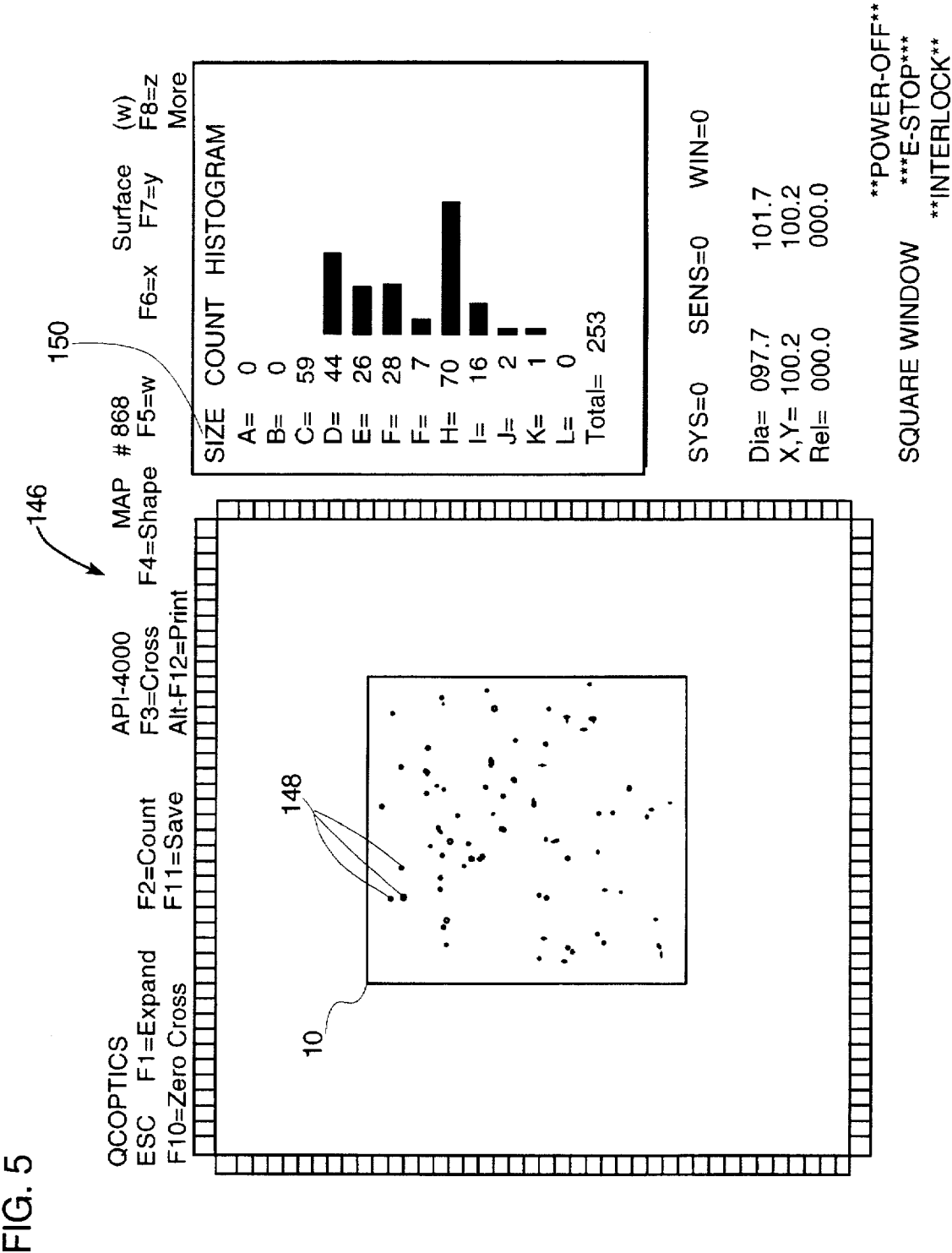
FIG. 5 is a schematic view of the representation of the locations, size and number of detected flaws produced on the display of the surface inspection system of this invention.

System 20, FIG. 2, is used to inspect photolithographic mask 10 according to this invention and when the inspection is completed, system 20 provides the operator with a computer generated map on display 22 (see FIG. 5) depicting the location, relative size, and number of all flaws (e.g. particles) detected on photolithographic mask 10, FIG. 1. The operator, or the system itself, then determines whether a particular photolithographic mask is suitable for use in a production run to produce thousands of semiconductor wafers in a stepper machine.

Inspection station 24 only detects particles as small as one micron but the inspection time is fairly fast, approximately one minute. As discussed in the background of invention, this inspection station may be a "API-3000" disclosed in U.S. Pat. No. 4,943,734. Recently developed inspection station 26, on the other hand, has a sensitivity of 0.25 microns but the complete inspection of a given photolithographic mask takes approximately 15 minutes.

In the invention of this application, it was realized that if the inspection of a given photolithographic mask at any time and at that at any station 24 or 26 reveals that the quality of the mask is below a preset quality threshold or thresholds, there is no need to continue the inspection of that mask. For example, if it is determined that during the inspection of a photolithographic mask at low resolution station 24 there are too many flaws of a particular size, there is no need to pursue a 15 minute inspection at high resolution station 26. Also, if during the first two minutes of an inspection at high resolution station 26 it is determined that there is a single particle in a very critical area on the photolithographic mask, there is no reason to continue inspection of the remainder of the photolithographic mask. In the surface inspection system 20 of this invention, terminator program 28 residing in master computer control data and storage subsystem 30 is programmed to monitor the complete inspection process for a breach of a preset inspection threshold stored in memory at 32 and in response halts the inspection thereby automatically ceasing any further inspection at one station and/or interrupting a transfer from one station to another.

Another feature of this invention is the ability to set a maximum number of detected flaws of a predetermined size to be displayed on monitor 22 thereby eliminating unwanted noise and providing a clear picture of the actual flaws detected to quality control personnel. A display threshold 83 is set before, during, or after the inspection based on the assumption that a certain number of particles of a particular size or sizes is indicative of noise or the chrome surface pattern—not flaws. Once this threshold is reached, display controller 80 discontinues mapping those size particles on display 22. Also, the operator input program can be used to partition the display 22 into several windows each having its own display threshold. The various components of system 20 are discussed as follows.

General System Components

Robot Load/Unload Station

Station 40 is robotic load/unload station 2 which includes plate gripper 42 for gripping plate 10 and placing it within plate holder 44 for inspection. Plate gripper 42 is also used to remove plate 10 after inspection of the primary chrome patterned surface is complete and to place plate 10 within plate holder 44 in an inverted position for inspection of the opposite non-patterned surface. Plate gripper 42 is positioned by robot translation stage 46 and robot rotation stage 48 which are under the control of robot controller 50. Robot control program 52 and computer control and data storage unit 30 drives robot controller 50.

Low Resolution Station

Station 24 is typically a glass/pellicle inspection station which is used to inspect the surface of pellicle 14 and it also may be used to inspect the second non-patterned surface of plate 10 which does not require very accurate inspection. Station 24 includes focusing stage 216 which is under control of computer control and data storage unit 30. Power supply and control unit 218 drives blue laser 220 to output a laser beam which is supplied to beam focusing optics 222, scanner 224, scan lens 226, beam splitter 228 and eventually to the surface of pellicle 14 to be scanned. Scanning encoder 230 and folding mirrors 232 and 234 are scanned with the scanning beam and provide computer control and data storage unit 137 with the beam position.

Normal scattering detector array 236 and back scattering detector array 238 provide electrical signals indicative of the normal and back scattered light scattered from the surface of pellicle 14 or the non-patterned surface of plate 10 to analog signal processor 240, digital signal processor 242, and ultimately to computer control and data storage unit 30. When scanning pellicle 14, back scattering detector array 238 is used to detect high intensity back scattered energy encountered when the beam illuminates the aluminum frame of the pellicle. The location of each position of the pellicle frame is stored and mapped in computer control and data storage unit 30. This pellicle frame map is used when plate 10 is translated to inspection station 26 to undergo inspection according to this invention as described below. At inspection station 26, when plate 10 is inspected, inspection data is automatically discarded at the locations where the pellicle frame is present and outside of the pellicle frame. Thus, the pellicle frame and areas outside of the pellicle frame are essentially masked out of the inspection process. This is very useful in that the pellicle frame and the areas outside of the pellicle frame, upon inspection, provide unnecessary information which would otherwise overload the detectors and the system memory.

Inspection station 24 also includes a reflectance detector 244 which is used to detect the amount of light reflected from the pellicle to provide a signal to computer control and data storage 30 to adjust the laser output to compensate for the attenuation of light by the pellicle.

After the pellicle is inspected at glass/pellicle inspection station 24, plate 10 is translated to inspection station 26 where the plate is inspected as described below. The translation of plate holder 44 is achieved by translation motor 246 under the control of translation motor controller 248 which is driven by computer control and data storage unit 30. The rotation of plate holder 44 is achieved by rotation motor 114 under the control of rotation motor controller 250 which is also driven by computer control and data storage unit 30.

Microscope Review Station

Microscope review station 27 is used by an operator to visually inspect any detected flaws. Station 27 includes a control keypad 262 which allows the operator to control the review process. The operator may review successive particles on display 22, change the illumination brightness and/or label each particle detected, among other options. Review microscope 264 includes microscope illuminator 266 and video camera 268 which supplies display 146 with a video image of the surface of plate 12. Microscope focusing stage 266 translates microscope 264 in the direction of arrows 267 by control key/pad and 262.

High Resolution Station

Inspection station 26 generates laser beam 25 which operates at two wavelengths, namely, 351 nm and 364 nm, generated by stationary laser source 105. Laser beam 25 passes through an expander in beam forming optics 104 converting beam 25 into an expanded beam. The expanded beam impinges upon the reflecting surface of off-axis parabolic mirror 31 which focuses the beam to a small spot on the surface of plate. Mirror 31 is adjusted via focusing actuator 33 which translates in the direction of arrows 33 to maintain the focus of the laser beam on the surface. Off-axis parabolic mirror 31 is positioned such that it forms a converging beam focussed at an inspection point at an angle of approximately 60° from normal to the surface of plate 10. Plate holder 44 is rotated and translation stage 26 translates such that the beam effectively traces a spiral path having a plurality of revolutions on the surface of plate 10. Plate 10 holder 14 is typically vertically oriented to hold plate 12 in a vertical position to minimize the amount of contamination of the plate by airborne particles.

Light scattered from point of inspection on the surface of plate 10 as a result of a flaw or a regular surface pattern is received by detectors 39 and 41. Light incident upon a regular surface pattern is scattered to produce a number angular regions of substantial intensity separated by a number of angular regions of very low intensity levels distributed fairly regularly about the pattern on the surface. Light incident upon a surface flaw, however, produces a fairly uniform high intensity scattering of light about the flaw. Thus, by placing detectors 39 and 41 in the regions where low levels of scattered light from patterns are expected, system 20, as described in detail below, can readily distinguish between flaws and surface patterns by determining the minimum detected intensity level from the detectors. If a very low level is detected at least by one of detectors 39 and 41, below a predetermined limit, no flaw is present, while if levels above the limit are detected by both detectors, a surface flaw is present. Although only two detectors are used in this configuration, this is not a necessary limitation of this invention, as any number of detectors greater than two could be used as long as at least some of them are located proximate the expected low scattering directions of the pattern scattering distribution.

The converging beam has an elliptical cross-section of approximately 2 by 5 microns. When the converging beam is projected upon the surface of plate 10, an enlarged elliptical beam spot is formed at the point of inspection. The projected beam spot on the surface of plate 12 is approximately 2 by 10 microns in size. Conventional inspection systems, e.g. inspection station 24, utilize a beam which produces a spot size between 15 and 50 microns. As discussed in the Background of Invention, a large spot size results in decreased resolution and sensitivity. Thus, by using an ultraviolet laser which produces a smaller beam spot sensitivity and resolution of inspection station 26 is greater than the sensitivity of station 24. Further, by using an ultraviolet laser having a shorter wavelength, the resolution is additionally increased.

In order to inspect the entire surface of plate 10 with the stationary converging beam, plate 10 is rotated in the direction of arrow 17, at 1800 rpm and translated in the direction of arrows 21 such that a spiral path of the converging beam is traced on the surface of plate 10. In order to insure adequate overlap of adjacent revolutions of spiral path the trace pitch (distance from the center of each beam revolution to the center of its adjacent revolutions) of the spiral is set at approximately 3 µm. By selecting a 3 µm pitch (the centers of successive revolutions are spaced 3 µm apart) with a 2×10 micrometer beam, adequate overlap is obtained as shown at the 80% intensity level of the beam. It is known from the gaussian profile of the converging beam that at 80% intensity, the beam width will be approximately 3.33 µm. Thus, by choosing a 3 µm pitch adequate overlap is insured and no portion of surface 10 between successive revolutions of a spiral trace is left uninspected.

Flaw Location and Size and Count Determination

Figure 3:
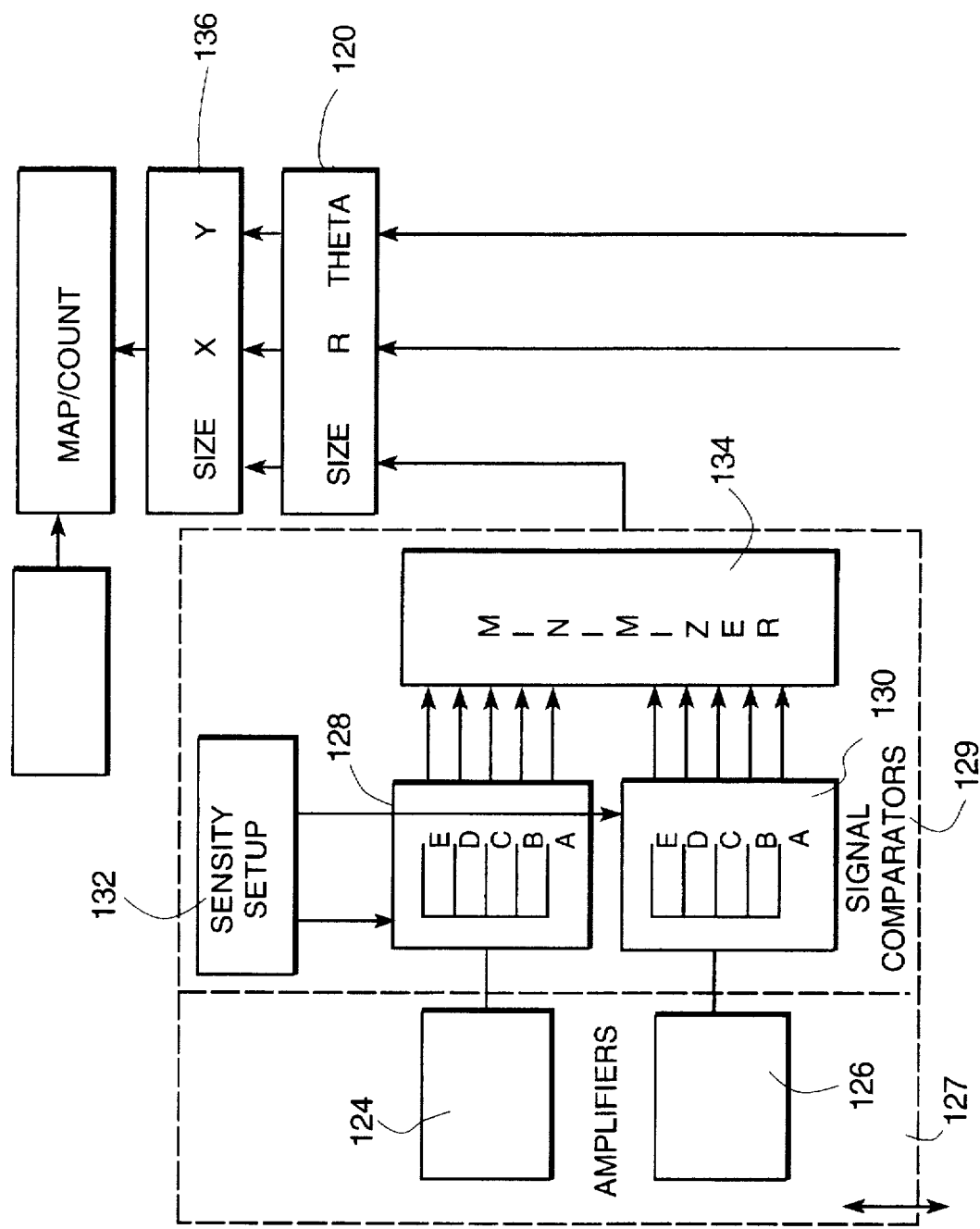
FIG. 3 is a schematic block diagram of the analog signal processing circuit shown in FIG. 2 for determining particle size.

The location and size of a detected flaw is determined first by detecting the level of the scattered light distribution received by detectors 39 and 41 from the ultraviolet illumination of a point of inspection on the surface of plate 10. Detectors 39 and 41 provide an electrical signal corresponding to the intensity of light detected over lines 121 and 122 to analog signal processing circuit 127. Circuit 127 includes amplifiers 124 and 126, FIG. 3. The amplified signals are provided to two sets of signal comparators 128 and 130 within digital signal processing circuit 129, FIG. 2. Comparators 128 and 130, FIG. 3, which may be LT1016 circuits produced by Linear Technology, each output a digital word to minimizer 134, which may be a 20V8 circuit produced by Lattice Semiconductor. A comparator output signal equal to zero indicates that neither detector 39 nor 41 detected an intensity level which is above the threshold level. Signals that exceed the threshold level produce different digital words that correspond to the size of the signal and hence the size of the flaw detected. In this example only five different flaw sizes (A–E) are shown, however, a greater number of sizes could be used. Sensitivity set-up circuit 132 enables the adjustment of the levels A–E so that an operator can vary the sensitivity level for different applications. The digital words corresponding to the signals detected from comparators 128 and 130 are provided to minimizer 134 which outputs the minimum intensity level detected by detectors 39 and 41. If the digital output from minimizer 134 is equal to zero, this indicates that a pattern (or nothing) was detected at that particular point on plate 10. A non-zero output indicates that a flaw is present and the data is provided to polar coordinate particle detector 120 which simultaneously receives the polar coordinates, R and Θ, of the location of the flaw detected from translational and rotational encoders 112 and 116, respectively, FIG. 2. The flaw size and the polar coordinates are provided to cartesian conversion program 136 within computer control and data storage unit 30, which converts the polar coordinates R and Θ to cartesian coordinates X and Y and receives the flaw size signal. Display controller 80 stores the position and size of each detected particle and keeps count of the total number of particles detected and the number of particles detected in each size category.

System Operation

Figure 4:
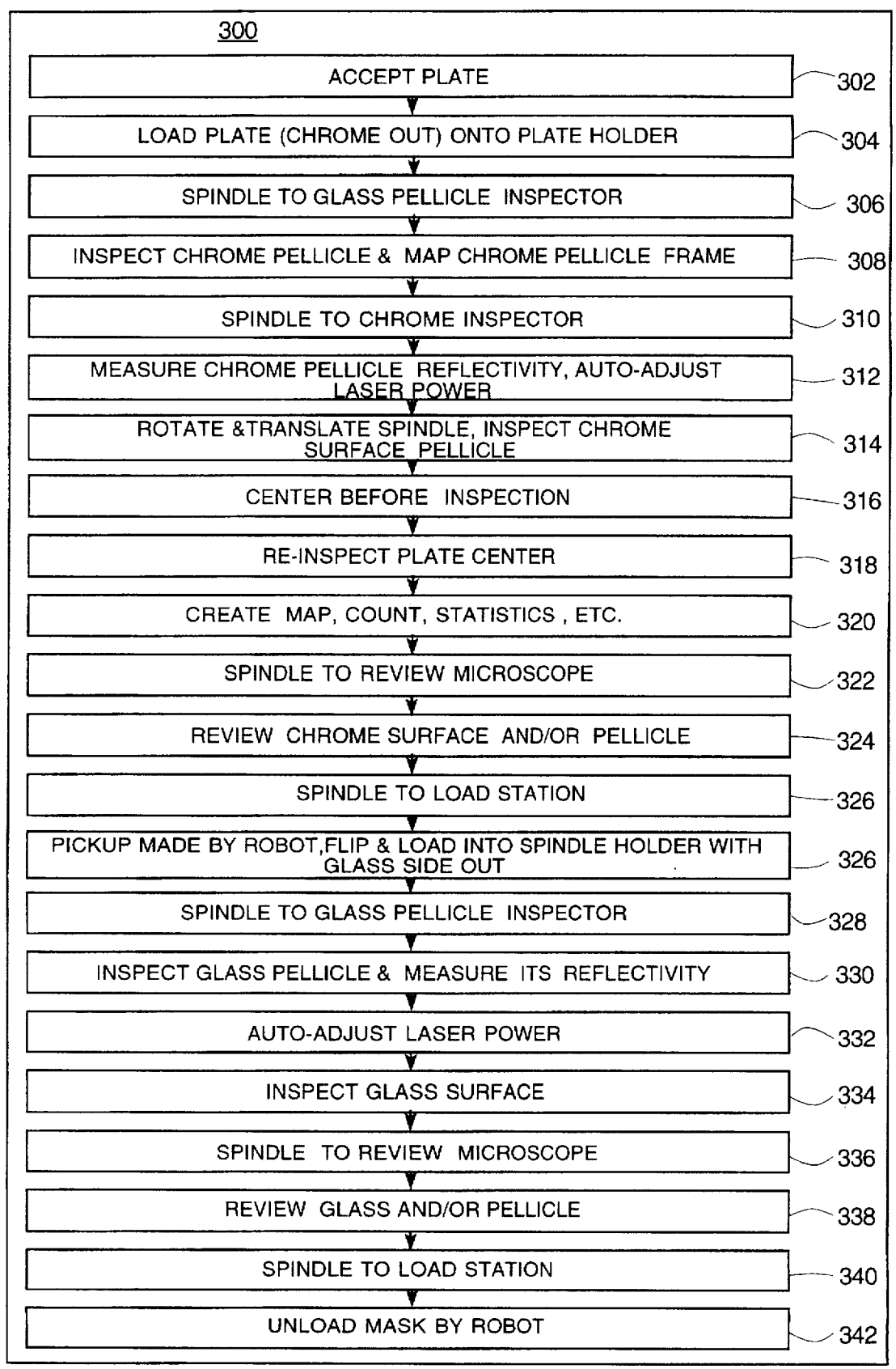
FIG. 4 is a flow chart depicting the inspection steps carried out automatically by the surface inspection system of this invention.

Flow chart 300, FIG. 4, delineates the steps accomplished in computer control and data storage unit 30, FIG. 2 for the inspection of a plate. In step 302 a plate is accepted by plate gripper 42, FIG. 2 and at step 304 the plate is loaded onto plate holder 44. Plate holder 44 is then translated to inspection station 24 at step 306 and at step 308 the chrome side pellicle is inspected and the pellicle frame locations (positions) are mapped. At step 310 plate holder 24 is translated to inspection station 100. At step 312 the pellicle reflectivity is measured and the laser power is compensated to adjust for the illumination energy attenuated by the pellicle. At step 314 plate 10 is simultaneously rotated and translated until a first beam path is traced and inspection of the surface of plate 10, excluding the portions covered by the pellicle frame, is completed. At step 316 plate 10 is reloaded and at step 318 the plate is reinspected. At step 320, a map of the flaw locations on the surface of plate 10 is created and stored within a computer control and data storage unit 33 and/or displayed on display 22. At step 322 the plate holder 44 and plate 19 are translated to microscope review stage 27 where at step 324, the chrome pattern surface of plate 10 and/or chrome side pellicle may be visually reviewed by the operator. At step 326 plate holder 44 and plate 10 are translated to load/unload station 40 when at step 326 the plate 10 is unloaded and reloaded with its second, non-patterned surface (glass side) facing up so it can be inspected. At step 328 plate 10 with its glass surface face up is translated to 24. At step 330 the pellicle covering the glass surface of plate 10 is inspected and its reflectivity is obtained. The laser power of glass/pellicle inspection station 24 is adjusted at step 332 to compensate for the light intensity attenuated by the pellicle and at step 334 the glass surface is inspected by glass/pellicle inspection station 24. Since the inspection of the underside surface of plate 10 need not be as accurately inspected, inspection can be performed at glass/pellicle inspection station 24. At step 336 plate 10 is translated to microscope review station 27 and at step 338 the glass surface of plate 10 and/or glass side pellicle are inspected under microscope 27. At step 340 plate 10 and plate holder 44 are translated to robotic load/unload station 40 and plate 10 is unloaded by plate gripper 42 at step 342.

Other configurations of multistation inspection systems and/or other inspection processing steps of system 30 are possible and robotic control program 52 can be programmed as required for a specific implementation. The result of a complete inspection is a computer generated map 146, FIG. 5 on display 22, FIG. 2.

After the entire surface of plate 10 has been inspected and the location and size of each flaw on the surface of plate 10 has been stored, a determination is made based on certain criteria provided by an operator-defined parameter list whether or not to accept or reject the particular plate under inspection. For example, if the total number of flaws detected exceeds a predetermined number or if a predetermined number of certain size flaws is exceeded then the plate is rejected.

Flaw Plotting

Operator input device 84 allows the operator to control exactly what is plotted on display 22. The computer program for plotting flaws on a CRT is as follows:

```
\                                              16:13 02-01-95
: POINT-mf \ COL xf(af) yf(bf) --, POINT AT Xf Yf (map units)
  2 ARGSf
  af Xmf->Xp
  bf Ymf->Yp
  POINT-crt ;              \ DRAW POINT USING PIX_LOGIC
: POINT-MAX-mf             \ col xf yf
  SET-MAX-crt              POINT-mf ;
: POINT-XOR-mf
  SET-XOR-crt              POINT-mf ;
-->
```

The operator can program display controller 80 to plot all flaws which are detected or controller 80 can be programmed to plot flaws according to predetermined criteria. For example, a display threshold for each size category can be set so that once a display threshold is reached, display control 80 automatically stops plotting flaws of that size on display 22, although it continues to count all flaws in each size category.

The operator can also program display control 80 to partition the display into a number of segments and then set an upper limit on the number of flaws to be plotted in each of the segments. Again, display control 80 will display only up to the display threshold set by the operator and once this display threshold is reached it will discontinue plotting the flaws but it will continue to count them and store them in memory 30. This operation is discussed in more detail below with reference to FIG. 9.

Figure 6:
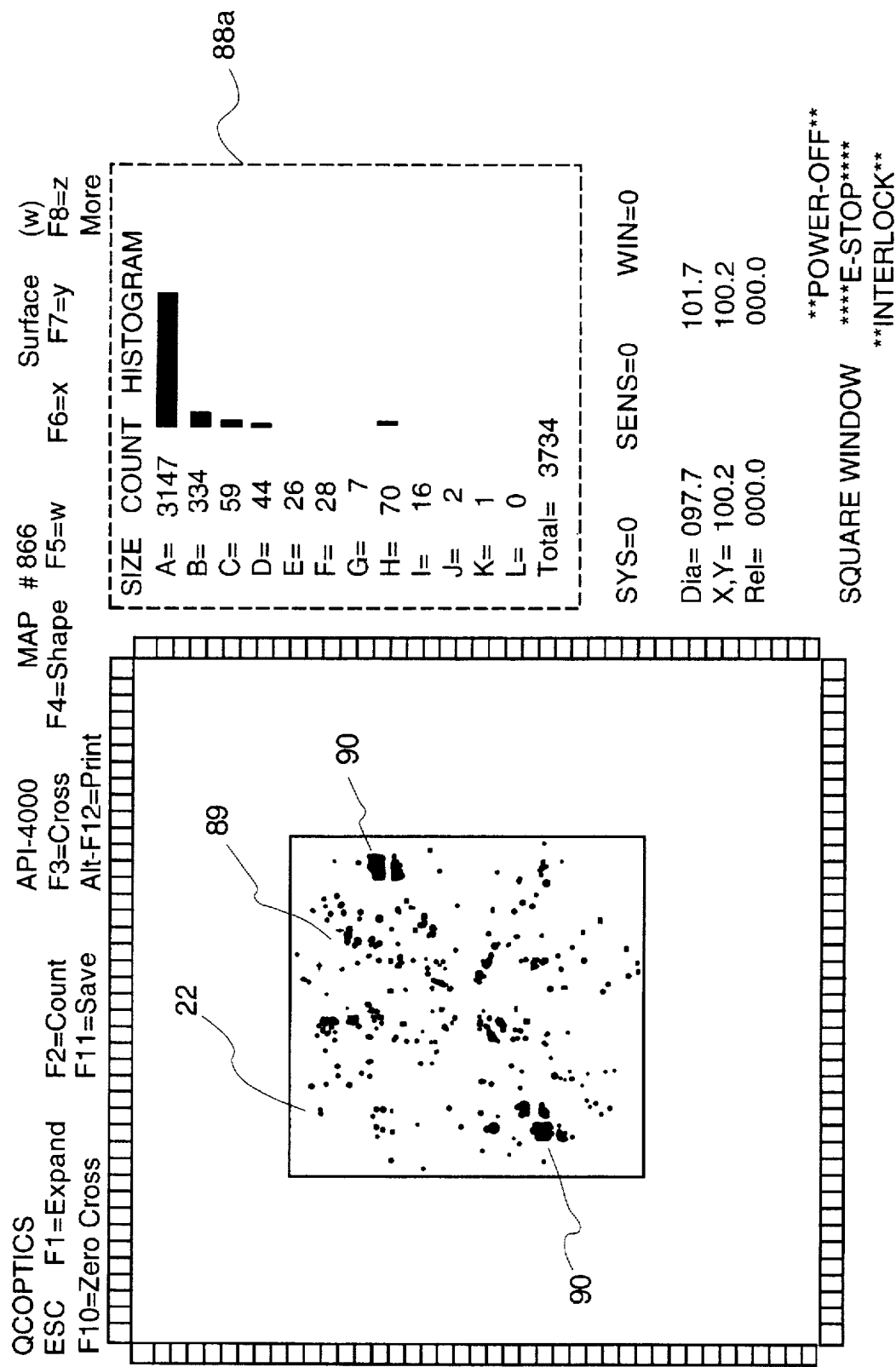
FIG. 6 is a schematic view of the monitor of the surface inspection system of this invention displaying all detected flaws.
Figure 7:
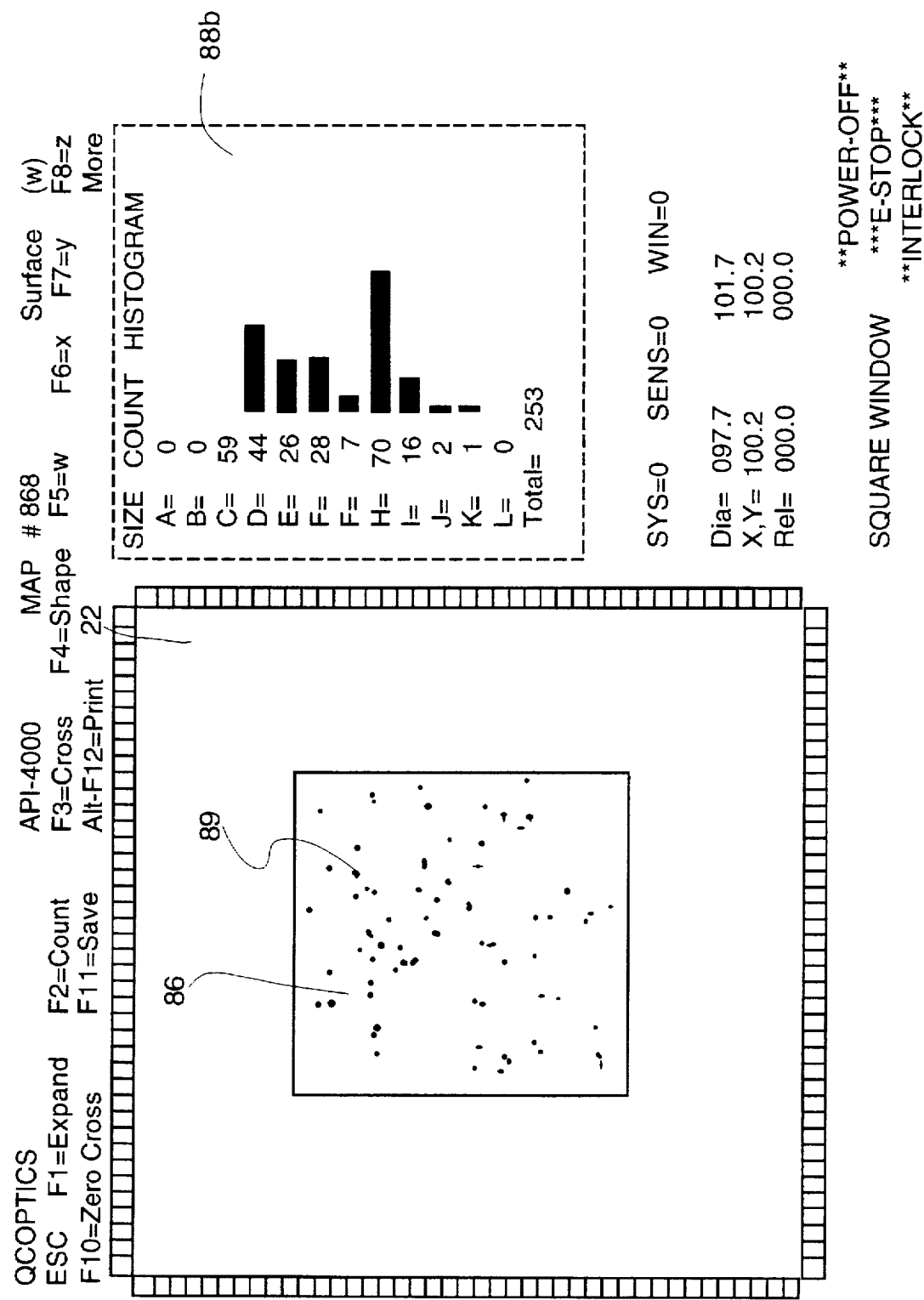
FIG. 7 is a schematic view of the monitor of FIG. 6 with flaws indicative of noise eliminated.

Display 22 is shown in more detail in FIGS. 6 and 7. In FIG. 6 there is shown a display in which all flaws detected during an inspection scan of a plate 10 are plotted. While some of the flaws shown on display 22 as indicated by reference 89 are actual flaws on the plate, groupings of what seem to be flaws as indicated by reference 90 represent noise as a result of diffraction of the inspection beam by the chrome pattern on plate 10. These patterns can be plainly seen by the operator when all of the flaws detected are plotted. As is shown in display area 88a, there is a listing of the number of flaws detected in each size category indicated by the letters A–L. Each letter represents an increasing amount of intensity detected by detectors 39 and 41, FIG. 2, with size A representing the smallest size flaw. On display screen 22, FIG. 6, each size is represented by a different color so that the operator can easily distinguish between sizes when viewing the display. The program for setting the different colors for each size is as follows:

```
143
      \ DRAW THE PALECT LEVEL INDICATOR              04:49 11-15-94
      : DRAW> 1 ARGS
        a 65 = IF DEF-A TS 1 - MSGcnty    TAB . " >" ELSE
```

-continued

```
    a 66 = IF DEF-B TS 1 - MSGcnty    1 + TAB . " >" ELSE
    a 67 = IF DEF-C TS 1 - MSGcnty    2 + TAB . " >" ELSE
    a 68 = IF DEF-D TS 1 - MSGcnty    3 + TAB . " >" ELSE
    a 69 = IF DEF-E TS 1 - MSGcnty    4 + TAB . " >" ELSE
    a 70 = IF DEF-F TS 1 - MSGcnty    5 + TAB . " >" ELSE
    a 71 = IF DEF-G TS 1 - MSGcnty    6 + TAB . " >" ELSE
    a 72 = IF DEF-H TS 1 - MSGcnty    7 + TAB . " >" ELSE
    a 73 = IF DEF-I TS 1 - MSGcnty    8 + TAB . " >" ELSE
    a 74 = IF DEF-J TS 1 - MSGcnty    9 + TAB . " >" ELSE
    a 75 = IF DEF-K TS 1 - MSGcnty   10 + TAB . " >" ELSE
    a 76 = IF DEF-L TS 1 - MSGcnty   11 + TAB . " >" THEN
        THEN THEN THEN THEN THEN THEN THEN THEN THEN THEN
    ; ->
ok
142
        \ DRAW THE DEFECT LEVEL INDICATOR              04:50 11-15-94
        : DEF-A   A-DAT   D-BAR  !   PAL#0 ;   \ SET DEFECT LEVEL FOR COUNT
        : DEF-B   B-DAT   D-BAR  !   PAL-B ;   \ SET PALETTE FOR COLOR
        : DEF-C   C-DAT   D-BAR  !   PAL-C ;
        : DEF-D   D-DAT   D-BAR  !   PAL-D ;
        : DEF-E   E-DAT   D-BAR  !   PAL-E ;
        : DEF-F   F-DAT   D-BAR  !   PAL-F ;
        : DEF-G   G-DAT   D-BAR  !   PAL-G ;
        : DEF-H   H-DAT   D-BAR  !   PAL-H ;
        : DEF-I   I-DAT   D-BAR  !   PAL-I ;
        : DEF-J   J-DAT   D-BAR  !   PAL-J ;
        : DEF-K   K-DAT   D-BAR  !   PAL-K ;
        : DEF-L   L-DAT   D-BAR  !   PAL-L ;
        -->
ok
5
        \                                              11:52 02-10-95
        HEX
        CREATE PAL-X   20 ALLOT \ VARIABLE
        : PAL#0       PAL-X SET-COUNTER \ ORIGINAL PALETTE
            00 CX! 01 CX! 02 CX! 03 CX! 04 CX! 05 CX! 14 CX! 07 CX!
            38 CX! 39 CX! 3A CX! 3B CX! 3C CX! 3D CX! 3E CX! 3F CX!
            PAL-X !PALETTE
        \ THE PALETTE MAPS A NUMBER TO A COLOR
        \ EXAMPLE:    # 14 IS YELLOW IF THE 15TH # IN PAL-CRT = 3E
        \             # 14 IS GREEN IF THE 15TH # IN PAL-CRT = 3A
        \ GRN=3A,RED=3C,YEL=3E,WHT=3F
        : NEW-PALETTE PAL-X SET-COUNTER \ CHANGES CRT YEL TO GRN
            00 CX! 01 CX! 02 CX! 03 CX! 04 CX! 05 CX! 14 CX! 07 CX!
            38 CX! 39 CX! 3A CX! 3B CX! 3C CX! 3D CX! 3A CX! 3F CX!
            PAL-X !PALETTE :          ( 3E)
        DECIMAL -->
ok
```

In the present invention, the operator can preset a display threshold: a size and upper count limit so that only the desired flaws are plotted on display 22. Alternatively, the operator can choose to allow flaws of all sizes to be plotted on the display and then set the display threshold to eliminate what the operator believes to be false flaws after he views the display.

If upon viewing the display shown in FIG. 6 the operator wishes to eliminate the pattern noise indicated by reference 90, since these are most likely false flaws caused by diffraction by the mask chrome surface pattern and the operator is not interested in this part of the display, the operator uses operator input device 84, FIG. 2, to inform display control 80 to not plot the size categories which make up noise 90. In display area 88a of FIG. 6 it can be seen that size categories A and B make up the majority of the defects mapped on display 22. Eliminating the false flaws is done by changing the palette of colors so that the unwanted colors, which represent the unwanted sizes, are black so that they do not show up on a black background of display 22. As can be seen in display area 88b, FIG. 7, sizes A and B have been set not to be plotted on display 22. Now only true flaws 89, etc. are shown and the total count of each size is shown in display area 88B. To re-display any eliminated size flaws, the palette is readjusted to its original color, which allows that size category to be seen on the display.

Figure 8:
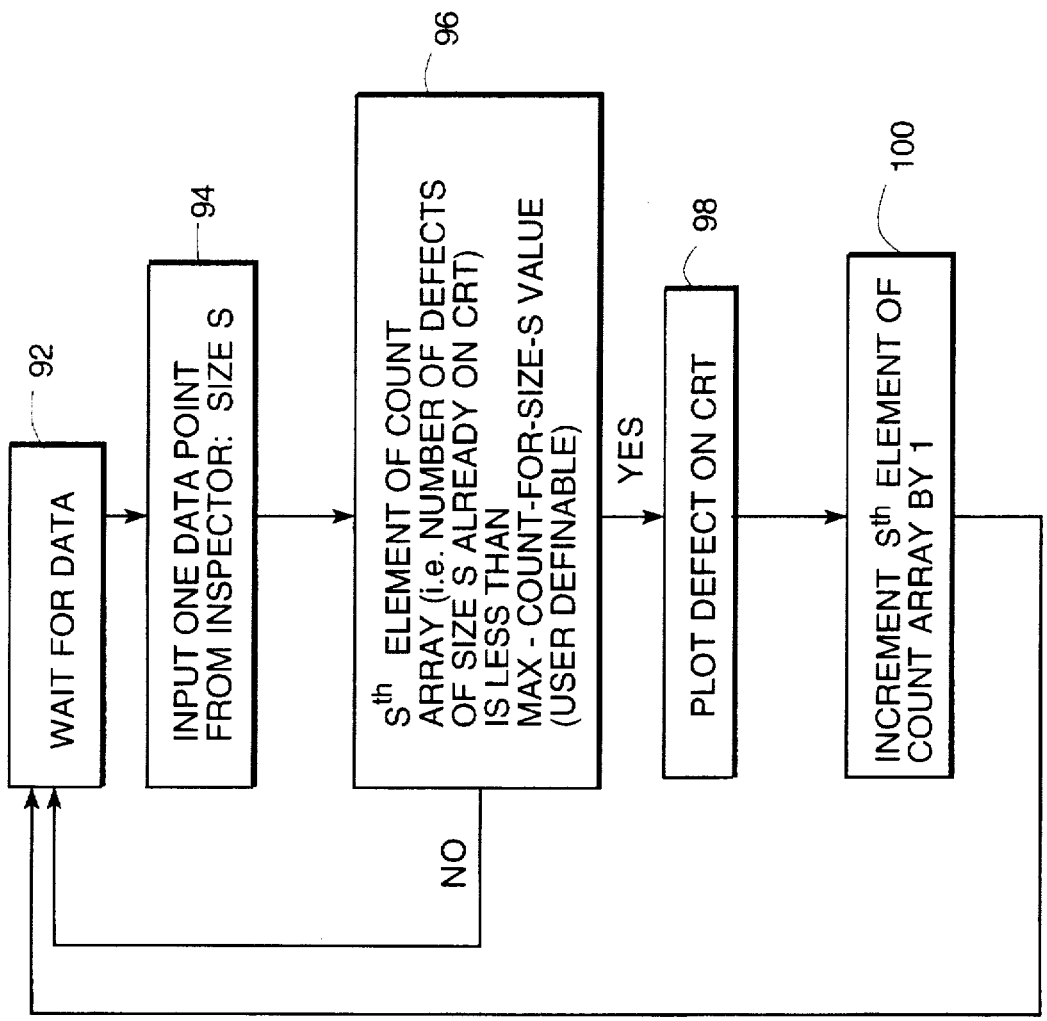
FIG. 8 is a flow chart of the operation of the display controller of FIG. 2.

In FIG. 8 there is shown a flow chart of the process which display controller 80 follows when the operator has present upper limits for the different size categories. In step 92, display controller 80 waits for flaw size and location data from signal processing circuits 127 and inspection station 26, FIG. 2 respectively. When this data is received, step 94, circuit 80 compares the number of defects previously plotted on display 22 with the display threshold set by the operator, step 96, and if the number of defects displayed is less then the threshold, controller 80 plots the flaw on display 22, step 98. When the processor plots the flaw on display 22, the count in that size category is incremented by one, step 100, the data is stored in memory 30 and the processor returns to step 92 to wait for incoming data. If the number of defects already plotted is equal to the threshold set by the operator, the controller 80 does not display any more flaws of that size, stores the flaw location and size data in memory 30 and then waits for more incoming data, step 92. The computer program which caries out this process is as follows:

```
                                            18:46 01-18-95
/
HEX
PROC (SIZE-OVERFLOW)?   \ AL = SIZE (0-15 dec)
    EBX PUSH EAX PUSH EDI PUSH
    EBX, # SIZE-TABLE    MOV    \ RUNNING TOTAL TABLE
    EDI, # MAX-SIZE-TABLE MOV   \ MAX LIMIT TABLE
    EAX, # F AND EAX, 2 SHL     \ LIMIT MAX DATA
                                  VALUE & MULT BY 4
        DWORD
        [EBX+EAX], # 1 ADD      \ INC SIZE BIN
        EBX, [EBX+EAX] MOV      \ PUT SIZE COUNT IN EBX
        EDI, [EDI+EAX] MOV      \ PUT LIMIT IN EDI
        EDI, EBX CMP            \ SET FLAGS
    EDI POP EAX POP EBX POP
    RET C; -->
ok
```

Figure 9:
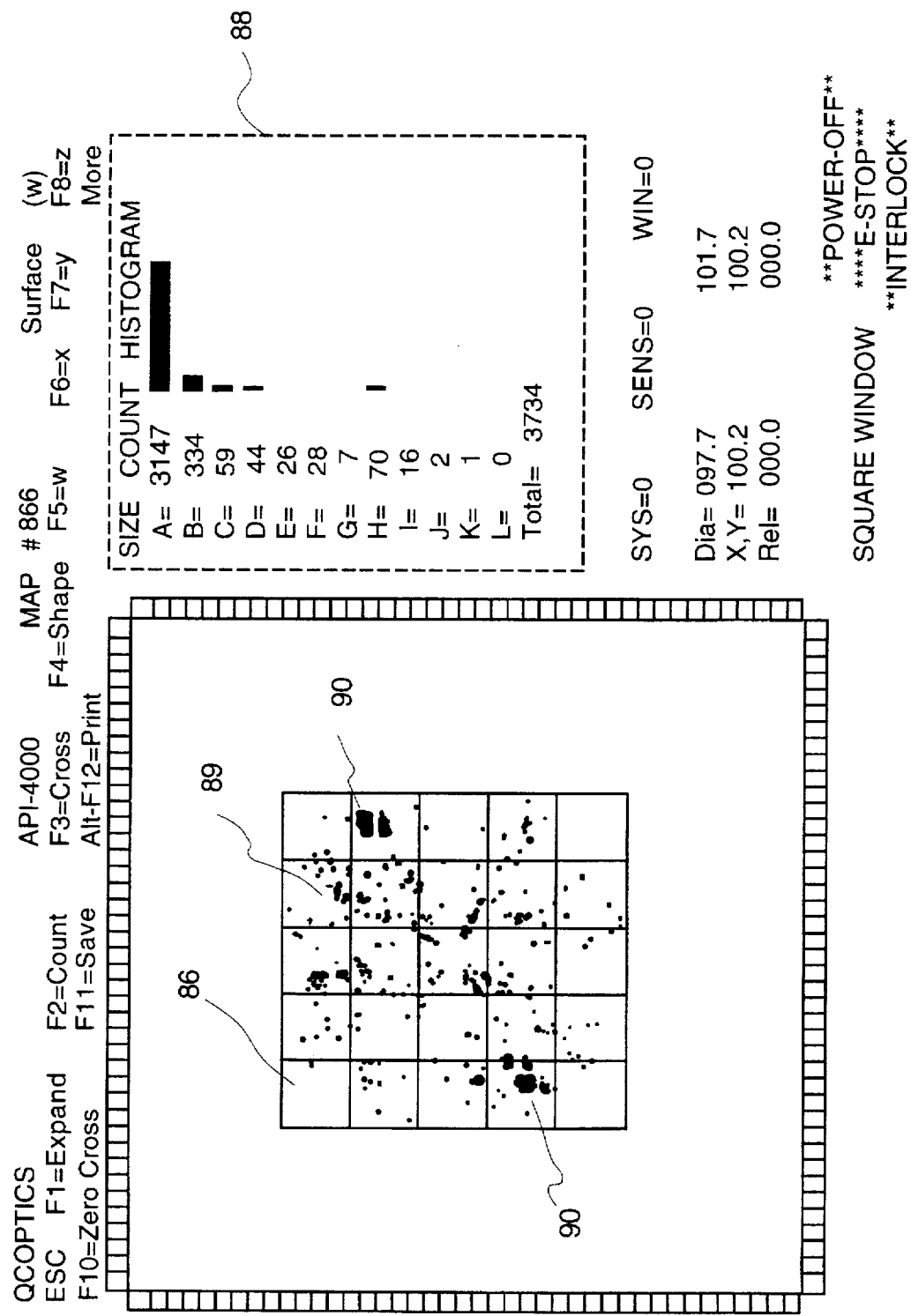
FIG. 9 is a schematic view of the monitor of FIG. 6 with the display area broken into windows each having a display threshold.

The display threshold can be set for any inspection station, 24 or 26, FIG. 2 at any time, before, during, or after an inspection. Operator input device 84 also allows the operator to divide display 22 into a series of windows as shown in FIG. 9. This is especially useful when the operator knows where a large number of false flaws will be detected due to pattern noise as shown by reference 90. In the example of FIG. 9, the operator could divide display 22 into several windows and then set an upper count limit for each size so that the pattern noise shown by reference 90 can be eliminated only in the windows which the operator desires. The operator would program display control 80 to eliminate, for example, sizes A and B from the particular window that the pattern noise falls into. The computer program which determines which window a flaw falls into is as follows:

```
                                            18:43 01-18-95
/
HEX
VARIABLE MAX-R-ARRAY 200 4 * ALLOT \ 512 WORDS (2048 BYTES)
\ STORES A TABLE OF MAX RADIUS VALUES TO PREVENT DATA OUTSIDE
\ OF WINDOW FROM BEING COLLECTED.
PROC (IN-WINDOW)? \ EDX=RADIUS (32 BIT), EBX =THETA (16 BIT MAX)
    EDI PUSH EBX PUSH EDX PUSH          \ SAVE REGS
    EDI, # MAX-R-ARRAY MOV              \ EDI POINTS TO ARRAY
    EBX, 5 SHR DWORD                    \ REDUCE RES TO 0-512 (4BYTES/W)
    EBX, # 7FC AND                      \ LIMIT THETA
    DWORD EBX, [EDI+EBX] MOV            \ EBX = MAX-R
    EDX, EBX CMP                        \ COMPARE R WITH MAX-R
    EDX POP EBX POP EDI POP             \ RESTORE REGS
    RET C;
    DECIMAL -->
ok
```

The program which monitors the flaw size and count data for each windows is as follows:

```
Screen # 18
\                                           19:13 01-18-95
DECIMAL
CODE IN-B->XYD      \ ---; MOVE DATA IN IN-B TO XYD (RAW FORM)
EBS PUSH ESI PUSH
EBI, # IN-B MOV       EBX, # 0 MOV      \ SOURCE (IN-B)
EDI, ' XYD 1 + MOV    EDI, RAW-PTR ADD  \ DESTINATION (XYD)
EDX, STAGE-POS-ENCum MOV                \ RADIUS -> EDX
BEGIN EAX, EAX XOR
    BYTE AL, [ESI+EBX] MOV              \ NEXT BYTE -> EAX
    (IN-WINDOW)? CALL    \ EDX=RAD(32 BIT), EBX=THETA(16 BIT)
    IF>                                 \ IF< (I.E., IN WINDOW)
        (SIZE-OVERFLOW)? CALL           \ ECX=1 IF OVERFLOW
    ELSE
        EAX, # 0 MOV EAX, # 1 CMP \ TO SKIP IF< not TEST
```

```
            THEN -->
Screen # 19
\      IN-B->XYD CONTINUED                    19:12 01-18-95
       IF< not    \ IF NO OVERFLOW & IN WINDOW
       AX, # 0 CMP                    \ ANY DATA?
       IF= not    AX, # 13 CMP        \ ANY DATA LESS THAN 13 ?
       IF<
       EDI, XYD-STOP CMP              \ MORE ROOM IN RAM?
       IF< not EBX, FIFO-SIZ MOV      \ IF NOT, SET TO EXIT LOOP
       ELSE  [EDI], EDX MOV           \ STORE RADIUS
             # XYSIZE [EDI], EBX MOV  \ STORE THETA
             # YXSIZE 2* [EDI], EAX MOV  \ STORE DATA
          DWORD RAW-PTR , # BYTES\DEF ADD  \ INC RAW-PTR VARIABLE
       THEN
       EDI, # BYTES/DEF ADD \ INC MEM POINTER
       THEN
      THEN
    THEN -->
Screen # 20
\      IN-B->XYD CONTINUED                    07:52 11-22-94
       EBX INC                        \ INC IN-B POINTER
       EBX, FIFO-SIZ CMP              \ END OF IN-B BUFFER ?
       UNTIL< not                     \ UPDATE RAW-XYD
    ESI POP EBX POP
    NEXT, C; -->
```

Inspection Threshold Value Determination

Another important feature of this invention is the ability to stop the inspection process if an inspection threshold is reached. An inspection threshold value is stored in inspection threshold value memory 32, FIG. 2 and when this value is exceeded determinator computer program 28 interrupts the inspection process delineated in FIG. 4. The threshold value may be a function of the size, location, and/or the number of particles detected at one inspection station or the size, location and/or the number of particles detected at each inspection station. The inspection threshold value may also be a cumulative value of the size, location, and/or number of particles detected at all inspection stations. A common inspection threshold value is a function of a number of particles of a particular size, for example, 300 particles of size B. Robot control program 52 operating on computer control and data storage subsystem 30 translates a photolithographic mask between inspection station 24, 27, and 26 in the order shown in the flow chart FIG. 4. If the inspection threshold stored in memory 32 is exceeded as determined by determinator 28, an interrupt signal may be sent to robot control program 52 to automatically interrupt the predetermined order whenever the threshold value is exceeded.

If the inspection at station 24 reveals that a quality threshold has been reached, determinator 28 will send an interrupt signal to robot control program 52 to prevent translation of a photolithographic mask to more precise inspection station 26.

The following is the actual computer code which is a part of the main data collection routine which moves a photolithographic mask, sets the laser power, collects data, converts polar coordinates to cartesian coordinates and the like. Including in this routine is an "exit data collection routine" which stops the data collection routine if the inspection threshold is reached.

```
  17
   \                                               14:15 02-05-95
      VARIABLE LAS-SET
     : EXIT-DATA-COLLECTION?
       STAGE-POS-ENCum @ STOP-n @ > \END ?
       RAW-FULL?    OR      \OUT OF MEMORY?
       ?TERMINAL    OR :    \KEY HIT ?

: DATA-CNT@
       RAW-PTR @ BYTES/DEF / ;
     : SHOW-DATA-STATUS       \USED DURING INSPECTION
       XY@   60 27 XYTAB          DATA-CNT@ 7 .R ." # OF DEFECTS"
             60 28 XYTAB     STAGE-POS-ENCum @ 7 .R ." LOCATION um"
             60 29 XYTAB             STOP-n @ 7 .R ." STOP LOC um"
             54 27 XYTAB        . "P=" LAS-SET @   .
       XYTAB ;
       ->
    ok
    ok
    ok
    ok
  23
   \                                              MPG 11:46 06-22-95
     : COLLECT-DATA-TEST
       ( BRAKE-OFF) TO-INSP-SITE-n
```

-continued

```
START-MOTORS-MOVING  SET-LASER-POWER  CHECK-LASER-POWER
INIT-FOR-XFER  INIT-XYD  FILL-MAX-R-ARRAY-IF  LASER-SHUTTER-OPEN
START-TRANS-MOVING-O    ENABLE-DATA-COLLECTION
BEGIN
   DATA-INPUT-CYCLE-IF
   SHOW-DATA-STATUS              \SHOW STATUS
   CONVERT-SOME-XYD  PLOT-NEW-XYDf   \PLOT REAL-TIME
   EXIT-DATA-COLLECTION?
UNTIL LASER-OFF
DISABLE-DATA-COLLECTION   STOP-TRANS-MOVING
PMTS-OFF   COMPS-OFF       SPIN-STOP   SHOW-DATA-STATUS
CONVERT-ALL-XYD            PLOT-NEW-XYDf
SORT-XYO-NEGf              CLR-SORT-MSG   O XEKEY !   ;  ->
```

Figure 10:
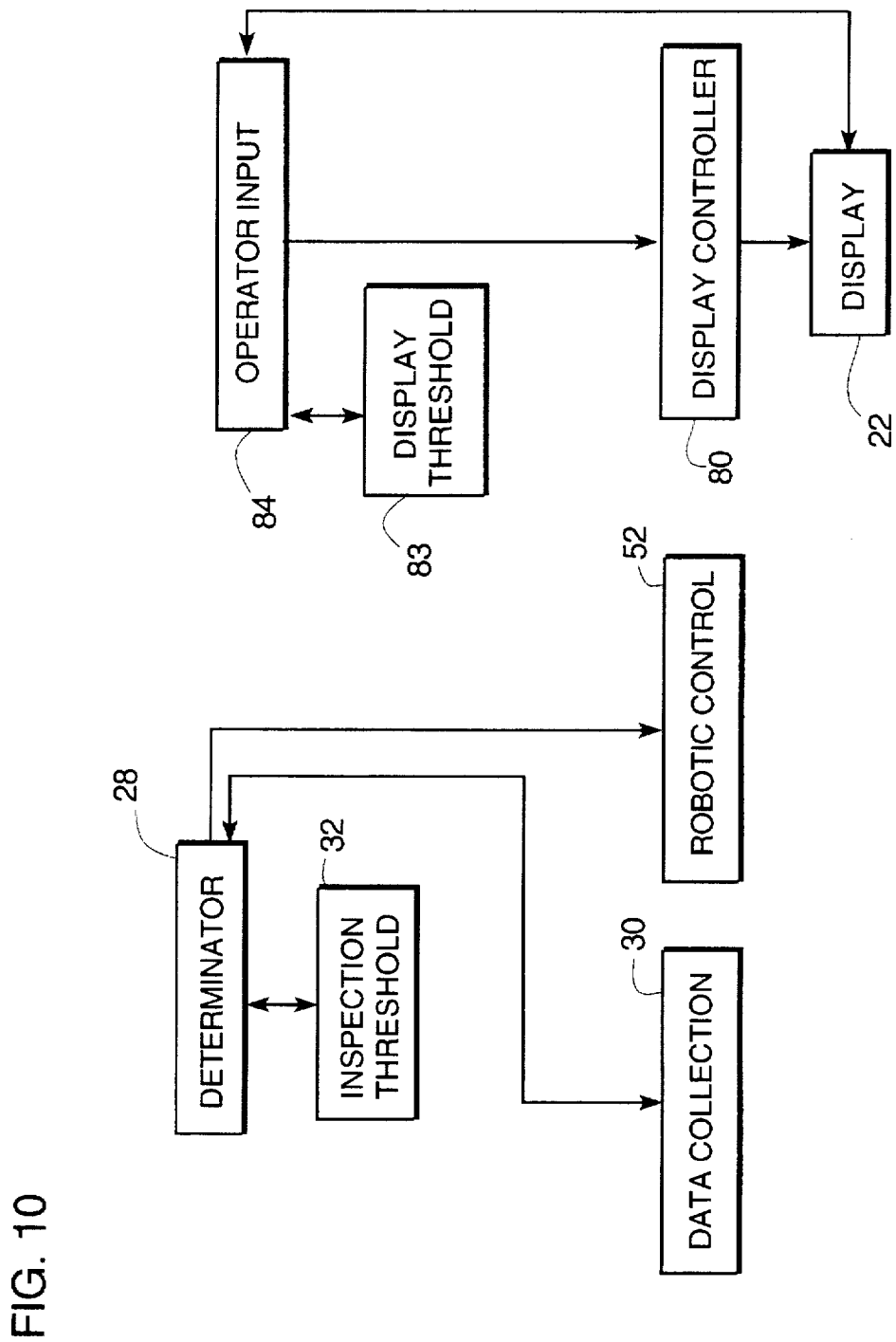
FIG. 10 is a functional block diagram of the primary subsystems of this invention for setting and monitoring an inspection threshold and for setting and monitoring a display threshold.

As shown in more detail in FIG. 10 determinator program 28 is responsive to one or more inspection threshold values stored in memory at 32 and monitors data collection program 30 to determine if the inspection threshold stored in memory 32 is breached. If so, determinator program 28 sends an interrupt signal to robotic control 52 to stop the inspection process and/or sends a signal to data collection program 30 to stop data collection. Determinator 28 can be programmed to stop the inspection at any station if a certain inspection threshold is reached (e.g. a particular number of particles of a particular size) and/or stop the transfer of a photolithoghraphic mask from low resolution inspection station 24 to high resolution inspection station 26 if the photolithographic mask does not pass the inspection at low resolution station 24.

Operator input program 84 is responsive to display threshold stored in memory at 83 to stop the display of certain size defects after the display threshold is reached by sending in signal to display controller 80 which drives display 22. The operator, using a menu on display 22, programs operator input program 84 before the inspection process begins, during the inspection process, or after the inspection process to monitor the size, number and position of detected particles or flaws and to take the appropriate action through display controller 80 to stop the display of and/or to remove the display of particles which exceed the display threshold. Also, as explained with reference to FIG. 9, the operator may use program 84 via a menu on display 22 to establish a number of windows and each or just one window may have its own display threshold. Note, however, that although specific features of the invention are shown in some drawings and not others, this is for convenience only as some feature may be combined with any or all of the other features in accordance with the invention. Other embodiments will occur to those skilled in the art and are within the following claims:

What is claimed is:

1. A surface inspection system comprising:
   a plurality of inspection stations in which a first said station has a first sensitivity and a first inspection time and a second said station has a second sensitivity and a second inspection time, the second sensitivity being greater than the first sensitivity, the second inspection time being longer than the first inspection time;
   means for translating a surface to be inspected to each station;
   means for storing at least one inspection threshold value;
   means for determining if said inspection threshold value has been exceeded and in response for outputting an inspection interrupt signal which stops the inspection.

2. The system of claim 1 in which a said inspection threshold value is a function of at least one of the size, location, and the number of particles detected at one inspection station.

3. The system of claim 1 in which said inspection threshold value is a function of at least one of the size, location, and number of particles detected at each inspection station.

4. The system of claim 1 in which said inspection threshold value is a function of a number of particles of a particular size.

5. The system of claim 1 in which said means for translating is programmable to translate a surface between inspection stations in a predetermined order.

6. The system of claim 5 in which said means for determining automatically interrupts said predetermined order whenever said inspection threshold value is exceeded.

7. The system of claim 1 in which said means for determining outputs an interrupt signal which prevents translation of a surface to said second station if said inspection threshold value is breached during inspection at said first station.

8. The system of claim 1 in which said means for determining outputs an interrupt signal which prevents further inspection of a surface at said second station when said inspection threshold value is breached during inspection at said second station.

9. The system of claim 1 in which said means for determining outputs an interrupt signal which prevents further inspection of a surface if said inspection threshold value is breached during inspection at one of said first and second stations.

10. A surface inspection method comprising:
    translating a surface to be inspected to a plurality of inspection stations;
    storing at least one inspection threshold value;
    determining if said inspection threshold value has been exceeded and in response outputting an inspection interrupt signal; and
    preventing further inspection of a surface at a station if said inspection threshold value is breached during inspection at said station.

11. The method of claim 10 in which a said inspection threshold value is a function of at least one of the size, location, and a number of particles detected at one inspection station.

12. The method of claim 10 in which said inspection threshold value is a function of at least one of the size, location, and a number of particles detected at each inspection station.

13. The method of claim 10 in which said inspection threshold value is a function of the number of particles of a particular size.

14. The method of claim 10 in which translating includes translating a surface between inspection stations in a predetermined order.

15. The method of claim 14 in which determining includes automatically interrupting said predetermined order whenever said inspection threshold value is exceeded.

16. The method of claim 10 in which determining includes outputting an interrupt signal which prevents translation of the surface to a second station if said inspection threshold value is breached during inspection at a first station.

17. A surface inspection system comprising:
- a first station with a first sensitivity and a first inspection time;
- a second station with a second sensitivity and a second inspection time, the second sensitivity being greater than the first sensitivity, the second inspection time being longer than the first inspection time;
- means for translating a surface to be inspected to the first station and thereafter to the second station;
- means for storing at least one inspection threshold value; and
- means for determining if said inspection threshold value has been exceed and in response for outputting an inspection interrupt signal which stops the inspection and prevents translation of the surface to said second station if said inspection threshold value is breached during inspection at said first station.

18. The system of claim 17 in which said means for determining outputs an interrupt signal which prevents further inspection of a surface at the second station when the inspection threshold value is breached during inspection at the second inspection station.

* * * * *